(12) United States Patent
Chung et al.

(10) Patent No.: US 10,155,022 B2
(45) Date of Patent: Dec. 18, 2018

(54) FAT ACCUMULATION INHIBITORY PEPTIDE AND PHARMACEUTICAL COMPOSITION FOR PREVENTING OR TREATING OBESITY CONTAINING THE SAME

(71) Applicants: SEOUL NATIONAL UNIVERSITY R&DB FOUNDATION, Seoul (KR); NANO INTELLIGENT BIOMEDICAL ENGINEERING CORPORATION CO., LTD., Chungcheongbuk-do (KR)

(72) Inventors: Chong-Pyoung Chung, Seoul (KR); Yoon Jeong Park, Seoul (KR); Jue-Yeon Lee, Gyeonggi-do (KR); Jin Sook Suh, Seoul (KR); In Ho Jo, Chungcheongnam-do (KR); Yoon Shin Park, Seoul (KR)

(73) Assignees: SEOUL NATIONAL UNIVERSITY R&DB FOUNDATION, Seoul (KR); NANO INTELLIGENT BIOMEDICAL ENGINEERING CORPORATION CO. LTD., Chungcheongbuk-Do (KR)

( * ) Notice: Subject to any disclaimer, the term of this patent is extended or adjusted under 35 U.S.C. 154(b) by 0 days.

(21) Appl. No.: 15/666,506

(22) Filed: Aug. 1, 2017

(65) Prior Publication Data
US 2017/0326201 A1    Nov. 16, 2017

Related U.S. Application Data

(63) Continuation of application No. 14/899,607, filed as application No. PCT/KR2015/007707 on Jul. 24, 2015, now abandoned.

(30) Foreign Application Priority Data

Jul. 24, 2014    (KR) .......................... 10-2014-0094182

(51) Int. Cl.
| | | |
|---|---|---|
| *A61K 38/08* | (2006.01) | |
| *A61K 38/16* | (2006.01) | |
| *A61K 38/00* | (2006.01) | |
| *A61K 9/00* | (2006.01) | |
| *C07K 14/00* | (2006.01) | |
| *C07K 7/06* | (2006.01) | |
| *C07K 7/00* | (2006.01) | |
| *A23L 33/18* | (2016.01) | |

(52) U.S. Cl.
CPC .............. *A61K 38/16* (2013.01); *A23L 33/18* (2016.08); *A61K 9/0019* (2013.01); *A61K 38/08* (2013.01); *C07K 7/06* (2013.01); *C07K 14/001* (2013.01); *A23V 2002/00* (2013.01)

(58) Field of Classification Search
CPC ...... A61K 38/08; A61K 38/16; A61K 9/0019; A61K 38/00; A61K 9/00; C07K 14/001; C07K 14/00; C07K 7/06; C07K 7/00
USPC ........ 514/21.4, 21.7, 1.1; 530/300, 326, 329
See application file for complete search history.

(56) References Cited

U.S. PATENT DOCUMENTS

| | | |
|---|---|---|
| 8,349,804 B2 | 1/2013 | Park et al. |
| 8,546,529 B2 | 10/2013 | Chung et al. |
| 2016/0296593 A1 | 10/2016 | Chung et al. |

FOREIGN PATENT DOCUMENTS

| | | |
|---|---|---|
| EP | 2615116 A1 | 7/2013 |
| KR | 100739528 B1 | 7/2007 |
| KR | 100894265 B1 | 5/2009 |
| KR | 1020130006194 A | 1/2013 |
| KR | 10-1348336 B1 | 12/2013 |
| WO | 2007089084 A1 | 8/2007 |
| WO | 2008150119 A1 | 12/2008 |

OTHER PUBLICATIONS

Choi, Y., et al., "Determination of osteogenic or adipogenic lineages in muscle-derived stem cells (MDSCs) by a collagen-binding peptide (CBP) derived from bone sialoprotein (BSP)", "Biochemical and Biophysical Research Communications", Feb. 10, 2012, pp. 326-332, vol. 419.
Hirsch, J., et al., "Adipose Tissue Cellularity in Human Obesity", "Clinics in Endocrinology and Metabolism", Jul. 1976, pp. 299-311, vol. 5, No. 2.
Otto, T., et al., "Adipose Development: From Stem Cell to Adipocyte", "Critical Reviews in Biochemistry and Molecular Biology", Jul.-Aug. 2005, pp. 229-242, vol. 40.
Shin, M., et al., "N-Formyl-Methionyl-Leucyl-Phenylalanine (fMLP) Promotes Osteoblast Differentiation via the N-Formyl Peptide Receptor 1-mediated Signaling Pathway in Human Mesenchymal Stem Cells from Bone Marrow", "The Journal of Biological Chemistry", May 13, 2011, pp. 17133-17143, vol. 286, No. 19.
"UniProtKB—D6R9C5 (D6R9C5_HUMAN)", Jul. 13, 2010, pp. 1-6 (as cited by Examiner in Dec. 9, 2016 Office Action issued in U.S. Appl. No. 14/899,607).

(Continued)

*Primary Examiner* — Julie Ha
(74) *Attorney, Agent, or Firm* — Hultquist, PLLC; Steven J. Hultquist (57) ABSTRACT

The disclosure relates to a fat accumulation inhibitory peptide which essentially comprises an amino acid sequence represented by SEQ ID NO: 1, a pharmaceutical composition for preventing or treating obesity, which contains the peptide, and a health functional food for preventing or alleviating obesity, which contains the peptide. The fat accumulation inhibitory peptide according to the present invention has the function of inhibiting the differentiation of mesenchymal stem cells into adipocytes to thereby inhibit the accumulation of adipose tissue. Thus, the peptide according to the present invention is highly useful for the prevention or treatment of obesity.

7 Claims, 5 Drawing Sheets
Specification includes a Sequence Listing.

(56) References Cited

OTHER PUBLICATIONS

Troke, R., et al., "The Future Role of Gut Hormones in the Treatment of Obesity", "Therapeutic Advances in Chronic Disease", 2014, pp. 4-14, vol. 5, No. 1.

*: Normal vs. treatment group
: OVX-PBS vs. treatment group

FIG. 4

*: Normal vs. treatment group
: OVX-PBS vs. treatment group

FIG. 5

*: Normal vs. treatment group
: OVX-PBS vs. treatment group

FIG. 6

\*: Normal vs. treatment group
\#: OVX-PBS vs. treatment group

FIG. 7

\*: Normal vs. treatment group
\#: OVX-PBS vs. treatment group

FAT ACCUMULATION INHIBITORY PEPTIDE AND PHARMACEUTICAL COMPOSITION FOR PREVENTING OR TREATING OBESITY CONTAINING THE SAME

CROSS-REFERENCE TO RELATED APPLICATIONS

This is a continuation under 35 U.S.C. § 120 of U.S. patent application Ser. No. 14/899,607 filed Dec. 18, 2015 for NOVEL FAT ACCUMULATION INHIBITORY PEPTIDE AND PHARMACEUTICAL COMPOSITION FOR PREVENTING OR TREATING OBESITY CONTAINING THE SAME, which in turn is a U.S. national phase under the provisions of 35 U.S.C. § 371 of International Patent Application No. PCT/KR2015/007707 filed Jul. 24, 2015, which in turn claims priority of Korean Patent Application No. 10-2014-0094182 filed Jul. 24, 2014. The disclosures of all such patent applications are hereby incorporated herein by reference in their respective entireties, for all purposes.

TECHNICAL FIELD

The present invention relates to a novel fat accumulation inhibitory peptide, a pharmaceutical composition for preventing or treating obesity, which contains the peptide, and a health functional food for preventing or alleviating obesity, which contains the peptide, and more particularly, to a fat accumulation inhibitory peptide which essentially comprises an amino acid sequence represented by SEQ ID NO: 1, a pharmaceutical composition for preventing or treating obesity, which contains the peptide, and a health functional food for preventing or alleviating obesity, which contains the peptide.

BACKGROUND ART

Currently, the obese population is gradually increasing. Obesity is a serious disease that causes diabetes, hyperlipidemia and cardiovascular diseases leading to death. Obesity is a serious health and social issue not only in advanced countries including the USA, but also in Korea. In the USA, costs for treating obesity account for about 6% of the total health-related costs, and in Korea, the obesity treatment market size is approaching one trillion Won (Korean currency). Obesity treatment agents are representative quality-of-life (QOL) improvers together with erectile dysfunction treatment agents and hair loss treatment agents.

Obesity refers to a condition in which adipocytes in the body proliferate and differentiate due to metabolic disorders, and thus fat is excessively accumulated. If energy absorption is higher than energy consumption, the number and volume of adipocytes increase, resulting in an increase in the mass of adipose tissue (Otto et al, Crit Rev Biochem Mol Biol., 40(4):229-242, 2005). Obesity at the cellular level is understood as the increase in number and volume of adipocytes caused by stimulation of the proliferation and differentiation of adipocytes (Hirsch et al, Clin Endocrinol Metab., 5(2): 299-311, 1976).

Current methods for treating obesity include drug-independent methods in which an excess of energy is consumed through exercise. In methods of treating obesity with drugs, there are used appetite suppressants that suppress appetite to limit calorie uptake, lipase inhibitors, bulk laxatives, energy stimulating agents, etc. The appetite suppressant sibutramine is a drug that was originally used as an antidepressant, and exhibits the effect of inhibiting the reuptake of serotonin in synapse to thereby provide quick satiety. However, this drug was reported to have various side effects, including cardiovascular action, central action, hepatic disorders and renal disorders. Orlistat acts to discharge fat from the body by inhibiting the function of the digestive enzyme lipase that degrades fat to help the absorption of fat in the body. However, Orlistat is known to have a serious side effect such as fecal incontinence, and the effect thereof cannot be guaranteed in the case of Koreans who live largely on carbohydrates.

Particularly, in the case of women, estrogen levels are lowered after the menopause while abdominal fat is accumulated. In addition, the risk of complications such as type 2 diabetes, cardiovascular diseases or osteoporosis also increases. Estrogen is an important hormone that is secreted from the female ovary and is involved in the development of uterine mucous membranes and mammary glands, the appearance of female secondary sex characters, the control of sexual cycles, and the maintenance of pregnancy. In recent years, it was reported that female hormones are involved in non-reproductive tissue (i.e., bone structure), cardiac blood vessels (lipid metabolism), dementia, colon cancer, teeth, macular degeneration, adipolysis, skin and collagen tissue production, etc., and thus play a very important role in women' health. In the case of hormone replace therapy (HRT) that was a potential menopausal symptom relief therapy for a while, HRT has a high risk of causing breast cancer, heart attack, stroke, cardiovascular diseases, etc., when it is applied over a long period of time. For this reason, the FDA announced to prohibit the long-term administration of female hormone drugs.

Thus, there is an urgent need for a new obesity treatment agent that cause less side effects and has guaranteed effects, and the demand for this obesity treatment agent is continuously increasing.

Accordingly, the present inventors have made extensive efforts to solve the above-described problems occurring in the art. As a result, the present inventors have developed a novel fat accumulation inhibitory peptide which has the function of inhibiting the differentiation of mesenchymal stem cells into adipocytes to thereby inhibit the accumulation of adipose tissue, similar to estrogen, and have found that the developed peptide has the effect of preventing or treating obesity, thereby completing the present invention.

DISCLOSURE OF INVENTION

It is an object of the present invention to provide a fat accumulation inhibitory peptide which has the function of inhibiting the differentiation of mesenchymal stem cells into adipocytes to thereby inhibit the accumulation of adipose tissue, similar to estrogen.

Another object of the present invention is to provide a pharmaceutical composition for preventing or treating obesity, and a health functional food for preventing or alleviating obesity, which contain the above fat accumulation inhibitory peptide.

Still another object of the present invention is to provide a method for preventing or treating obesity, which comprises administering the above pharmaceutical composition containing the fat accumulation inhibitory peptide.

Yet another object of the present invention is to provide the use of the above pharmaceutical composition containing the fat accumulation inhibitory peptide, for the prevention or treatment of obesity.

To achieve the above objects, the present invention provides a fat accumulation inhibitory peptide which essentially comprises an amino acid sequence represented by SEQ ID NO: 1.

The present invention also provides a pharmaceutical composition for preventing or treating obesity, and a health functional food for preventing or alleviating obesity, which contain the above fat accumulation inhibitory peptide.

The present invention also provides a method for preventing or treating obesity, which comprises administering the above pharmaceutical composition containing the fat accumulation inhibitory peptide.

The present invention also provides the use of the above pharmaceutical composition containing the fat accumulation inhibitory peptide, for the prevention or treatment of obesity.

BRIEF DESCRIPTION OF THE DRAWINGS

FIGS. 1A and 1B show the inhibition of differentiation of mesenchymal stem cells into adipocytes by the fat accumulation inhibitory peptide according to the present invention. Specifically.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, a novel fat accumulation inhibitory peptide was prepared, and mice were treated with the prepared peptide in order to examine the effects of the peptide on the inhibition of adipocyte differentiation and fat accumulation. As a result, it was found that the fat accumulation inhibitory peptide has the effect of inhibiting fat accumulation, and thus can be used as an obesity treatment agent.

In one aspect, the present invention is directed to a fat accumulation inhibitory peptide which essentially comprises an amino acid sequence represented by the following SEQ ID NO: 1:

SEQ ID NO 1: YGLRSKS

In the present invention, the fat accumulation inhibitory peptide may comprise an amino acid sequence represented by the following SEQ ID NO 2:

SEQ ID NO 2: YGLRSKSKKFRRPDIQYPDAT.

In the present invention, the fat accumulation inhibitory peptide may act to inhibit the differentiation of mesenchymal stem cells into adipocytes.

In another aspect, the present invention is directed to a pharmaceutical composition for preventing or treating obesity, which contain the above fat accumulation inhibitory peptide.

In still another aspect, the present invention is directed to a method for preventing or treating obesity, which comprises administering the above pharmaceutical composition containing the fat accumulation inhibitory peptide.

In yet another aspect, the present invention is directed to the use of the above pharmaceutical composition containing the fat accumulation inhibitory peptide, for the prevention or treatment of obesity.

As used herein, the term "composition" is intended to include not only a product containing a specific component but also any product made directly or indirectly by the combination of a specific component.

In the present invention, obesity may be caused by estrogen deficiency.

In the present invention, the pharmaceutical composition may further comprise a pharmaceutically acceptable carrier. The carrier pharmaceutically acceptable may be at least one selected from the group consisting of physiological saline, sterile water, Ringer's solution, buffered saline, dextrose solution, maltodextrin solution, glycerol, and ethanol, but is not limited thereto.

In the present invention, the pharmaceutical composition may further contain at least one additive selected from the group consisting of an excipient, a buffer, an antimicrobial preservative, a surfactant, an antioxidant, a tonicity adjuster, a preservative, a thickener, and a viscosity modifier, but is not limited thereto.

In the present invention, the pharmaceutical composition may be formulated for oral administration, injection administration or in the form of a gelling agent for local transplantation, but is not limited thereto. The composition of the present invention may be prepared into a suitable formulation using a known technique (Joseph Price Remington, *Remington's Pharmaceutical Science,* 17th edition, Mack Publishing Company, Easton Pa.).

The pharmaceutical composition for preventing or treating obesity according to the present invention can be administered through routes that are usually used in the medical field. The composition of the present invention is preferably administered parenterally. The composition according to the present invention may be administered, for example, orally, intravenously, intramuscularly, intraarterially, intramedullarily, intradually, intracardially, transdermally, subcutaneously, intraperitoneally, intrarectally, sublingually or topically.

In the present invention, the gelling agent for local transplantation comprises a synthetic polymer such as polylacticglycolic acid, poloxamer or propylene glycol, or a natural polymer such as collagen, alginic acid, propylene glycol alginic acid, chondroitin sulfate or chitosan, but is not limited to thereto.

The dose of the pharmaceutical composition for preventing or treating obesity according to the present invention may vary depending on the patient's weight, age, sex, health condition and diet, the time of administration, the mode of administration, excretion rate, the severity of the disease, or the like, and can be easily determined by those skilled in the art in consideration of the above factors.

The pharmaceutical composition of the present invention may be administered as an individual therapeutic agent or in combination with other therapeutic agents, and may be administered sequentially or simultaneously with conventional therapeutic agents.

In the present invention, the fat accumulation inhibitory peptide may be administered in an amount of preferably 1-60 mg, more preferably 3-30 mg, per kg of body weight of a subject to be treated.

In a further aspect, the present invention is directed to a health functional food for preventing or alleviating obesity, which contains the above fat accumulation inhibitory peptide.

As used herein, the term "health functional food" refers to a food is prepared and processed from raw materials or components having functionality useful for the human body pursuant to the law No. 6722 on the health functional food, or refers to a food that is taken for the purpose of controlling nutrients with respect to the structure and function of the human body or obtaining the effects useful for the health purposes such as physiologically functional purpose.

The health functional food according to the present invention may be formulated into a typical health functional food preparation known in the art. The health functional food may be prepared in the form of granules, tablets, pills, suspensions, emulsions, syrups, chewing gums, teas, jellies, various beverages, drinks, alcoholic beverages or the like. There is no particular limitation in the kind of the health functional food.

The health functional food according to the present invention may be any suitable galenical form for administration to the animal body including the human body, more specifically, any conventional form for oral administration, for example, food or feed, food or feed additives and adjuvants, enhanced food or feed, a solid form such as tablets, pills, granules, capsules and foam formulations, or a liquid form such as solutions, suspensions, emulsions, drinks and pastes. The composition of the present invention may contain nutrients, vitamins, electrolytes, sweeteners, colorants, organic acids, preservatives, etc. These additives may be used independently or in combination.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Synthesis of Fat Accumulation Inhibitory Peptide

A peptide represented by the following SEQ ID NO: 2 was synthesized from the C-terminus by an F-moc solid phase chemical synthesis method using a peptide synthesizer:

SEQ ID NO 2: YGLRSKSKKFRRPDIQYPDAT

The synthesized peptide sequence was separated from resin, washed, freeze-dried, and then purified by liquid chromatography. The molecular weight of the purified peptide was analyzed by MALDI.

Example 2

Adipocyte Differentiation Inhibitory Effect of Fat Accumulation Inhibitory Peptide Using mesenchymal stem cells (MSCs), the effect of the fat accumulation inhibitory peptide, prepared in Example 1, on adipocyte differentiation, was studied.

Mesenchymal stem cells (MSCs) were cultured in DMEM containing 1% antibiotic-antimycotic and 10% FBS, and were stored. Next, the cells were cultured in adipocyte differentiation induction medium (DMEM containing 10% FBS, 10 μM dexamethasone, 0.5 mM methyl-isobutylxanthine, 10 μg/ml insulin, 10 mM indomethacin, and 1% antibiotic-antimycotic) for 3 days, and were cultured in adipocyte differentiation induction medium (DMEM containing 10 μg/ml insulin, 10% FBS, and 1% antibiotic-antimycotic) for 3 days. The cells were culture for 14 days while the medium was replaced in the above order, thereby inducing differentiation of the cells. During the culture, a mixture of 95% air and 5% $CO_2$ was continuously supplied while a humidity of 100% and a temperature of 37° C. were maintained. The culture for differentiation was performed for a total of 14 days, and the peptide prepared in Example 1 was added whenever the medium was replaced. The peptide was added at concentrations of 0, 10, 100 and 200 μg/mL.

The cells cultured in the differentiation medium were washed with PBS and fixed with 10% formalin for 1 hour. 30% Oil red O solution diluted with 60% isopropanol was added to the cells which were then incubated at room temperature for 10 minutes. The cells were washed with purified water and observed with an optical microscope. After observation, isopropanol was added to dissolve the formed fat, and the absorbance at 510 nm was measured.

Figure 1A:
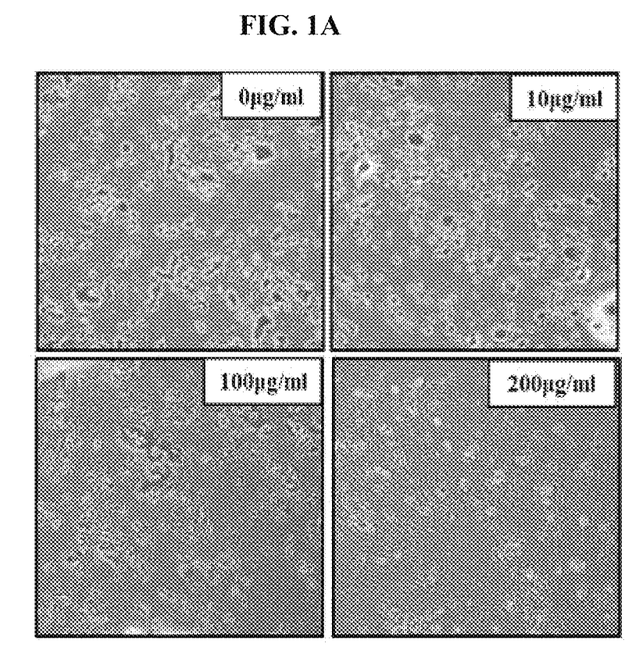
FIG. 1A is an image of adipocytes stained with Oil Red O.
Figure 1B:
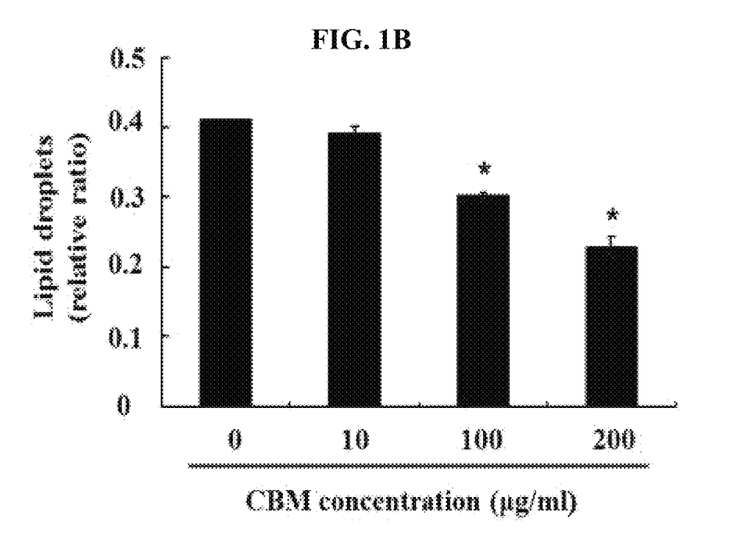
FIG. 1B shows the absorbance of free Oil Red O.

As a result, it could be seen that the differentiation of the mesenchymal stem cells into adipocytes was increased by the adipocyte differentiation medium (FIGS. 1A and 1B). In addition, it could be microscopically observed that, as the concentration of the peptide used to treat the cells increased, the accumulation of the fat stained with Oil red O decreased (FIG. 1A). Furthermore, when the produced fat was dissolved and the absorbance at 510 nm was measured, it could be seen that, as the concentration of the peptide increased, the absorbance decreased (FIG. 1B).

In addition, in the same manner as described above, mesenchymal stem cells were treated with the peptide prepared in Example 1. RNA was extracted from the cells and subjected to reverse transcription polymerase chain reaction (RT-PCR) using primers for glyceraldehyde-3-phosphate dehydrogenase (GAPDH) which is a control, and adipocyte protein 2 (aP2) and peroxisome proliferators activated receptor γ (PPARγ), which are adipocyte differentiation markers. The PCR products were electrophoresed on agarose gel in order to compare the expression levels of the control and the differentiation markers.

Figure 2:
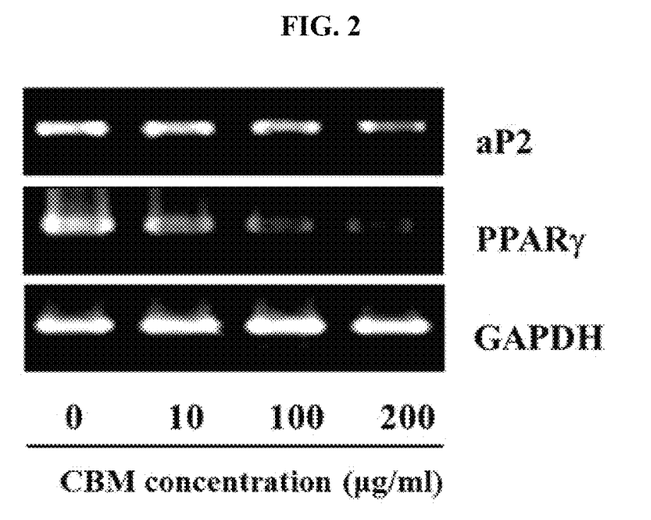
FIG. 2 shows the inhibition of differentiation of mesenchymal stem cells into adipocytes by the fat accumulation inhibitory peptide according to the present invention, and shows the results of electrophoresis of PCR products obtained in Example 2.

As a result, it could be seen that, as the concentration of the peptide used to treat the cells increased, the expression of the control GAPDH gene did not change, but the expression of the adipocyte differentiation marker genes (aP2 and PPARγ) decreased (FIG. 2).

Example 3

Fat Accumulation Inhibitory and Toxic Effects of Fat Accumulation Inhibitory Peptide ICR mice (Orient Bio, Korea) were purchased and acclimated, and the ovary was removed from the mice to induce estrogen deficiency, thereby inducing bone loss and an increase in the body weight of the mice. For ovariectomy, 6-week-old ICR mice were generally anesthetized by intramuscularly injecting a mixture of 10 mg/kg of xylazine (Rompun®, Bayer, Korea) and 100 mg/kg of ketamine (Ketalar®, Yuhan Corp., Korea) into the femoral region of the mice. The ovary present below both kidneys was carefully removed, and the mice were sutured according to a conventional method and injected intramuscularly with 3 mg/kg of gentamicin (Gentamicin®, Choongwae Pharma Corp., Korea), and then kept. From 3 months after ovariectomy, the peptide prepared in Example 1 was administered intraabdominally to the mice twice a week for a total of 8 weeks. The test animals were divided into 7 test groups as shown in Table 1 below, and the change in body weight and the fat accumulation of the mice were measured.

TABLE 1

| | | Sham (Pseudo-OVX)-PBS | Sham (Pseudo-OVX)-HP | OVX | | |
|---|---|---|---|---|---|---|
| | Normal | | | Control | LP | HP |
| Treatment materials (concentration, μg/25 g mice) | PBS | PBS | Peptide of SEQ ID NO: 2 (600 μg) | PBS | Peptide of SEQ ID NO: 2 (60 μg) | Peptide of SEQ ID NO: 2 (600 μg) |
| Number (heads) | 10 | 5 | 5 | 10 | 10 | 10 |

[Normal: normal group; Sham (Pseudo-OVX): non-ovariectomized test group; OVX: ovariectomized test group; Control: control group; LP: low-concentration peptide (60 μg/25 g mouse); HP: high-concentration peptide (600 μg/25 g mouse)]

Figure 3:
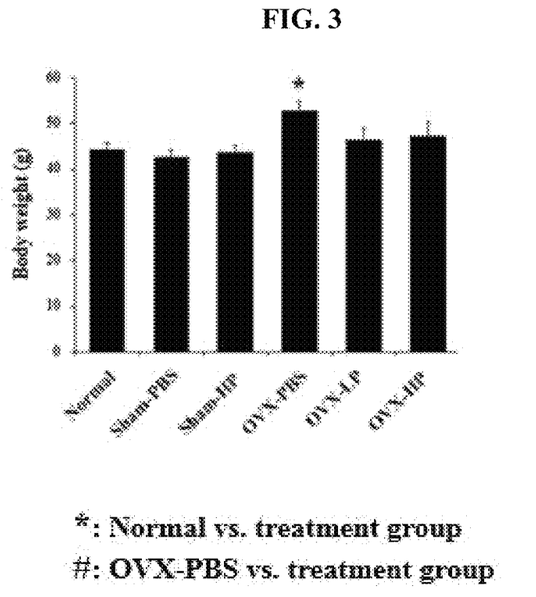
FIG. 3 shows the results of measuring the change in body weight caused by the fat accumulation inhibitory peptide according to the present invention, in Example 3.
Figure 4:
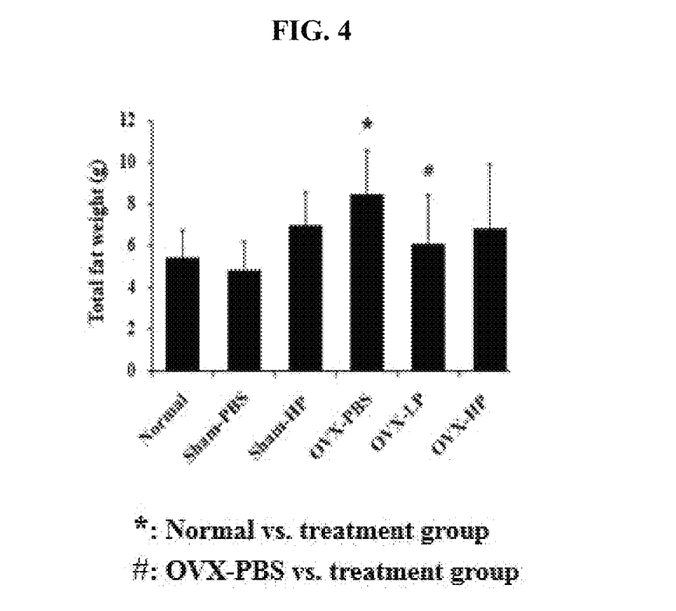
FIG. 4 shows the results of measuring the change in total fat weight caused by the fat accumulation inhibitory peptide according to the present invention, in Example 3.
Figure 5:
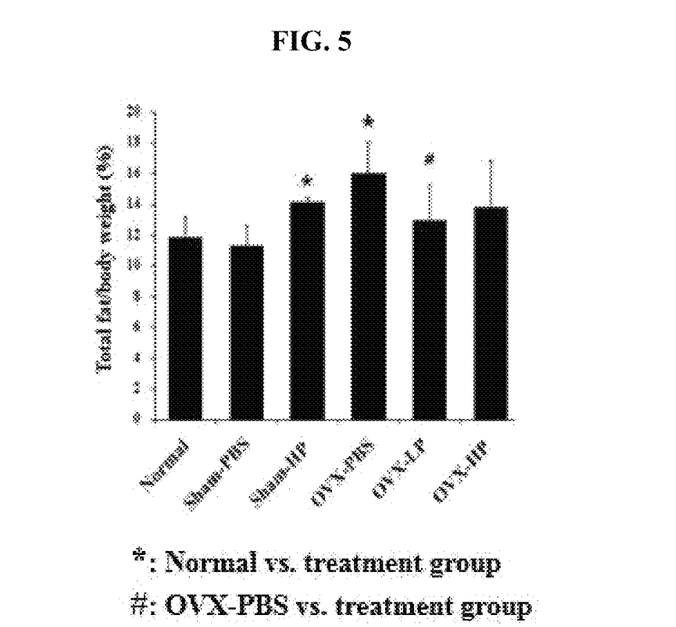
FIG. 5 shows the results of measuring the change in total fat/body weight caused by the fat accumulation inhibitory peptide according to the present invention, in Example 3.

When the change in the body weight of the mice was observed, it could be seen that the body weight and total fat weight of the ovariectomized test group increased and that the OVX-PBS group showed a significant increase in the body weight compared to the normal group. In addition, it could be seen that the total fat weight and the total fat/body weight were significantly higher in the OVX-PBS group than in the normal group, but significantly decreased in the test group treated with the peptide, suggesting that the peptide inhibits fat accumulation (FIGS. 3 to 5).

Figure 6:
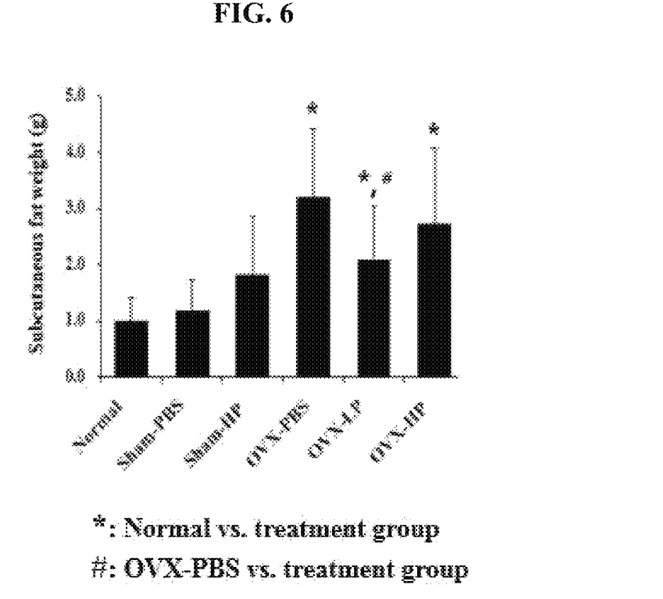
FIG. 6 shows the results of measuring the change in subcutaneous fat weight caused by the fat accumulation inhibitory peptide according to the present invention, in Example 3.
Figure 7:
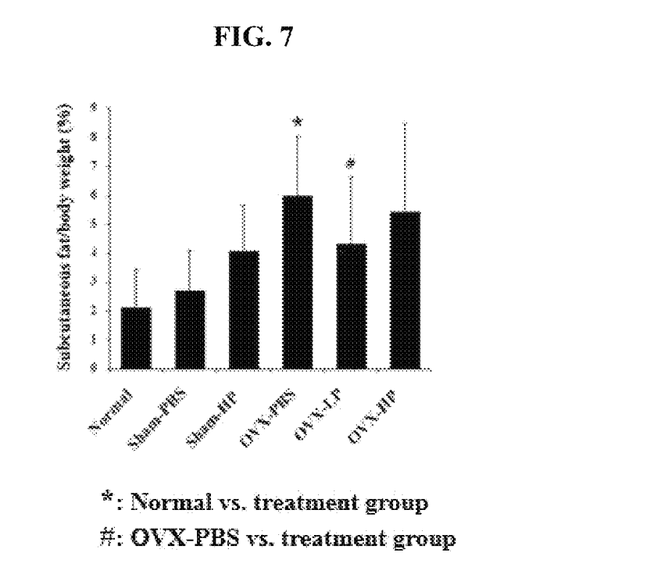
FIG. 7 shows the results of measuring the change in subcutaneous fat/body weight caused by the fat accumulation inhibitory peptide according to the present invention, in Example 3.

When the change in subcutaneous fat weight of the mice was observed, it could be seen that the subcutaneous fat weight changed more greatly than the total fat weight. Also, it could be seen that, in the ovariectomized test group, the subcutaneous fat weight significantly increased, but in the test group treated with the peptide, the subcutaneous fat weight decreased (FIGS. 6 and 7).

Figure 8:
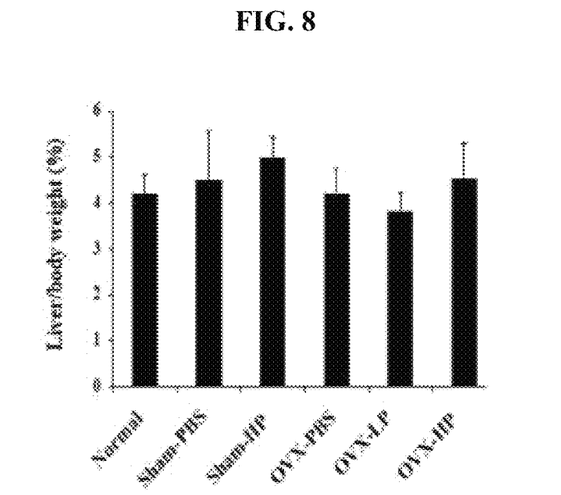
FIG. 8 shows the results of measuring the change in liver/body weight caused by the fat accumulation inhibitory peptide according to the present invention, in Example 3.
Figure 9:
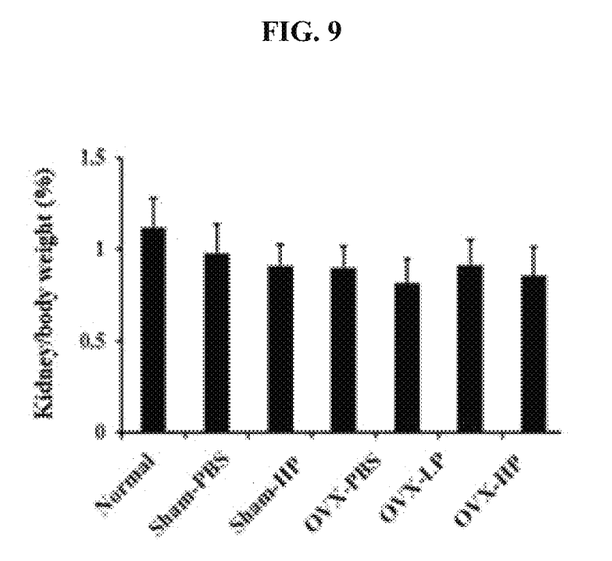
FIG. 9 shows the results of measuring the change in kidney/body weight caused by the fat accumulation inhibitory peptide according to the present invention, in Example 3.

In addition, as the indices of the hepatotoxicity and nephrotoxicity of the peptide, the weights of the liver and kidney of the mice were measured after autopsy. As a result, it could be seen that the weights of liver and kidney/body weight of the test group treated with the peptide were all similar to those of the normal group, suggesting that the hepatotoxicity and nephrotoxicity of the peptide were insignificant (FIGS. 8 and 9).

INDUSTRIAL APPLICABILITY

As described above, the fat accumulation inhibitory peptide according to the present invention has the function of inhibiting the differentiation of mesenchymal stem cells into adipocytes to thereby inhibit the accumulation of adipose tissue, similar to estrogen. Thus, the peptide according to the present invention is highly useful for the prevention or treatment of obesity.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating obesity, comprising administering a pharmaceutical composition which comprises the amino acid sequence represented by SEQ ID NO: 1 to a subject in need thereof.

2. The method of claim 1, wherein the obesity is obesity caused by estrogen deficiency.

3. The method of claim 1, wherein the pharmaceutical composition is administered by oral administration, injection administration, or local transplantation in the form of a gelling agent.

4. The method of claim 3, wherein the gelling agent comprises a synthetic polymer or a natural polymer.

5. The method of claim 4, wherein the synthetic polymer is any one selected from the group consisting of polylacticglycolic acid, poloxamer, and propylene glycol.

6. The method of claim 4, wherein the natural polymer is any one selected from the group consisting of collagen, alginic acid, propylene glycol alginic acid, chondroitin sulfate, and chitosan.

7. The method of claim 1, wherein the pharmaceutical composition is administered in an amount of 1-60 mg per kg of body weight of the subject in need thereof.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: peptide for inhibiting fat accumulation

<400> SEQUENCE: 1

Tyr Gly Leu Arg Ser Lys Ser
1               5

<210> SEQ ID NO 2
<211> LENGTH: 21
<212> TYPE: PRT
<213> ORGANISM: Artificial Sequence
<220> FEATURE:
<223> OTHER INFORMATION: peptide for inhibiting fat accumulation

<400> SEQUENCE: 2

Tyr Gly Leu Arg Ser Lys Ser Lys Lys Phe Arg Arg Pro Asp Ile Gln
1               5                   10                  15

Tyr Pro Asp Ala Thr
            20
```